(12) United States Patent
Suri et al.

(10) Patent No.: US 12,394,052 B2
(45) Date of Patent: Aug. 19, 2025

(54) SYSTEMS AND METHODS FOR DENTAL IMAGE ANALYSIS

(71) Applicant: VELMENI, Inc., Sunnyvale, CA (US)

(72) Inventors: Mini Suri, Sunnyvale, CA (US); Sohaib Laraba, Ghlin (BE); Alan Friedel, Hollywood, FL (US); Y. Samata, Andhra Pradesh (IN); Elias Ennadifi, Mons (BE); Nour Islam Mokhtari, Muret (FR); Housseyne Nadour, Grenoble (FR); Poonam Gupta, Winter Garden, FL (US); Tin Luu, Washington, DC (US)

(73) Assignee: VELMENI, INC., Sunnyvale, CA (US)

( * ) Notice: Subject to any disclaimer, the term of this patent is extended or adjusted under 35 U.S.C. 154(b) by 0 days.

(21) Appl. No.: 18/231,520

(22) Filed: Aug. 8, 2023

(65) Prior Publication Data
US 2024/0046456 A1     Feb. 8, 2024

Related U.S. Application Data

(60) Provisional application No. 63/396,013, filed on Aug. 8, 2022.

(51) Int. Cl.
*G06T 7/00*     (2017.01)
*A61B 6/51*     (2024.01)
(Continued)

(52) U.S. Cl.
CPC ............. *G06T 7/0012* (2013.01); *A61B 6/51* (2024.01); *G06T 7/11* (2017.01); *G06T 7/73* (2017.01);
(Continued)

(58) Field of Classification Search
CPC . G06T 7/0012; G06T 7/11; G06T 7/73; G06T 11/00; G06T 2207/10116; G06T 2207/20081; G06T 2207/20084; G06T 2207/30036; G06T 2210/12; G06T 2210/41; A61B 6/463; A61B 6/468; A61B 6/51; A61B 6/5217; G06V 10/25;
(Continued)

(56) References Cited

U.S. PATENT DOCUMENTS 10,932,890 B1   3/2021   Sant et al.
10,937,108 B1   3/2021   Tabak et al.
(Continued)

OTHER PUBLICATIONS

Lin et al., "Tooth Numbering and Condition Recognition on Dental Panoramic Radiograph Images Using CNNs", in IEEE Access, vol. 9, pp. 166008-166026, 2021, doi: 10.1109/ACCESS.2021.3136026 (Year: 2021).*

(Continued)

*Primary Examiner* — Nay A Maung
*Assistant Examiner* — Jose M Torres
(74) *Attorney, Agent, or Firm* — George Likourezos; Carter, DeLuca & Farrell LLP

(57) ABSTRACT

Systems and methods for analyzing dental radiographs use deep neural network architectures, model training procedures and data processing method for automated dental charting and condition detection. The systems and methods produce detailed outputs that are comprehensive analyses of dental radiographs attributing detected conditions to particular teeth.

19 Claims, 13 Drawing Sheets

(51) Int. Cl.
  *G06T 7/11* (2017.01)
  *G06T 7/73* (2017.01)
  *G06T 11/00* (2006.01)
  *G06V 10/764* (2022.01)
  *G06V 10/82* (2022.01)
  *G16H 15/00* (2018.01)

(52) U.S. Cl.
  CPC ............ *G06T 11/00* (2013.01); *G06V 10/764* (2022.01); *G06V 10/82* (2022.01); *G16H 15/00* (2018.01); *G06T 2207/10116* (2013.01); *G06T 2207/20084* (2013.01); *G06T 2207/30036* (2013.01); *G06T 2210/12* (2013.01); *G06T 2210/41* (2013.01)

(58) Field of Classification Search
  CPC .. G06V 10/764; G06V 10/82; G06V 2201/03; G16H 15/00; G16H 30/40; G16H 40/67; G16H 50/20; G16H 50/70
  See application file for complete search history.

(56) References Cited

U.S. PATENT DOCUMENTS

| | | | |
|---|---|---|---|
| 10,984,529 | B2 | 4/2021 | Cambron et al. |
| 10,991,091 | B2 | 4/2021 | Ezhov et al. |
| 11,158,046 | B2 | 10/2021 | Jelicich et al. |
| 11,189,028 | B1 | 11/2021 | Kearney et al. |
| 11,217,350 | B2 | 1/2022 | Kearney et al. |
| 11,276,151 | B2 | 3/2022 | Kearney et al. |
| 11,311,247 | B2 | 4/2022 | Kearney et al. |
| 11,348,237 | B2 | 5/2022 | Kearney et al. |
| 11,357,604 | B2 | 6/2022 | Kearney et al. |
| 11,366,985 | B2 | 6/2022 | Kearney et al. |
| 11,367,188 | B2 | 6/2022 | Kearney et al. |
| 11,398,013 | B2 | 7/2022 | Kearney et al. |
| 2018/0078347 | A1* | 3/2018 | Falkel ................ G16H 30/40 |
| 2019/0180443 | A1* | 6/2019 | Xue .................... G06T 7/13 |
| 2019/0222176 | A1 | 7/2019 | Khlat |
| 2020/0066391 | A1 | 2/2020 | Sachdeva et al. |
| 2020/0122261 | A1 | 4/2020 | Knoener et al. |
| 2020/0146646 | A1* | 5/2020 | Tuzoff .................. G06T 7/11 |
| 2020/0175681 | A1 | 6/2020 | Ezhov et al. |
| 2020/0305808 | A1* | 10/2020 | Ezhov ................ G16H 50/20 |
| 2020/0342539 | A1 | 10/2020 | Doney |
| 2020/0410649 | A1* | 12/2020 | Kearney ............. G06T 7/0012 |
| 2021/0073977 | A1 | 3/2021 | Carter et al. |
| 2021/0074061 | A1 | 3/2021 | Brown et al. |
| 2021/0074425 | A1* | 3/2021 | Carter .................. G06N 20/00 |
| 2021/0217170 | A1 | 7/2021 | Ezhov et al. |
| 2021/0224919 | A1 | 7/2021 | Tabak et al. |
| 2021/0233233 | A1* | 7/2021 | Jelicich ................ G16H 40/67 |
| 2021/0327000 | A1 | 10/2021 | Tabak et al. |
| 2021/0338387 | A1 | 11/2021 | Inam et al. |
| 2021/0343400 | A1 | 11/2021 | Inam et al. |
| 2021/0383480 | A1 | 12/2021 | Tabak et al. |
| 2022/0084267 | A1 | 3/2022 | Ezhov et al. |
| 2022/0189611 | A1 | 6/2022 | Farkash et al. |
| 2022/0192590 | A1 | 6/2022 | Hillen |

OTHER PUBLICATIONS

Baan, et al., "Fusion of intra-oral scans in cone-beam computed tomography scans," Clinical Oral Investigations (2021).
Lin, et al., "Tooth Numbering and Condition Recognition on Dental Panoramic Radiograph Images Using CNNs," IEEE Access (vol. 9), Dec. 24, 2021.
PCT/US2023/029755, Search report.
PCT/US2023/029755, Written Opinion.
International Preliminary Report on Patentability issued by the International Bureau of WIPO in connection with International Application No. PCT/US2023/029755, dated Feb. 4, 2025.

* cited by examiner

SYSTEMS AND METHODS FOR DENTAL IMAGE ANALYSIS

CROSS-REFERENCES

This application claims priority of U.S. provisional application Ser. No. 63/396,013 filed Aug. 8, 2022 and titled "SYSTEMS AND METHODS FOR INTRAORAL IMAGE ANALYSIS" by present inventors.

BACKGROUND

In the field of dentistry, dental radiographs are a tool for the identification of various conditions that may not be easily detectable through clinical examination. These radiographs provide detailed insights into the oral health of a patient, enabling the detection of issues ranging from cavities and decay to more complex conditions such as bone loss or hidden dental structures. However, the process of analyzing these radiographs and documenting the findings can be a time-consuming and labor-intensive task for dental professionals. This is particularly true when the analysis involves a large number of radiographs or complex cases with multiple dental conditions.

The challenge lies not only in the interpretation of the radiographs but also in the accurate charting and recording of the findings. Manual charting can be prone to errors and inconsistencies, and it can be a significant drain on the resources of a dental practice. Moreover, the complexity of dental structures, which often have irregular forms and curvatures, adds to the difficulty of the task.

In recent years, advancements in technology have led to the development of automated systems for dental imaging analysis. These systems typically employ image recognition techniques to identify and locate various objects in an image. However, conventional image recognition systems often use bounding boxes to indicate the location of detected objects. While this approach can identify the presence and rough location of an object, it does not provide a precise delineation of the object's boundaries, especially for non-rectangular objects such as teeth.

There is a need for more refined detection and image processing methods in the automation of dental imaging analysis. Specifically, there is a need for methods that not only identify and locate objects in an image but also accurately delineate the boundaries of these objects. Such methods would provide a more accurate representation of the shapes and sizes of the objects, which is particularly important in the context of dental radiographs.

It remains desirable to have improved methods and systems for automation of dental imaging analysis.

SUMMARY

The present invention is directed to systems and methods for automated dental imaging analysis. The systems and methods leverage advanced techniques such as object segmentation to provide a more accurate and efficient analysis of dental radiographs. The systems and methods aim to address the limitations of existing methods, enhancing the accuracy of dental charting, and reducing the time and effort required for the task.

In a first embodiment, a system for analyzing a dental radiograph includes a tooth numbering module configured to receive at least one dental radiograph and to locate and label teeth present in the at least one dental radiograph, a condition detector module configured to receive the at least one dental radiograph and to identify and locate conditions in the at least one dental radiograph, and, a merging module configured to receive a first output from the tooth numbering module and a second output from the condition detector module, and to merge the first and second outputs to form a report having labeled teeth with conditions identified and located on specific teeth.

In an alternative embodiment, the system further includes an image type classifier to determine the type of the dental radiograph.

In a first alternative arrangement, the condition detector locates identified conditions with both bounding boxes and masks. In a second alternative arrangement, the condition detector module uses a plurality of condition detector models where each condition detector model is configures and developed for a particular dental radiograph type. In a third alternative arrangement, the condition detector module uses an object detection model to identify conditions present in the at least one dental radiograph. In a fourth alternative arrangement, the condition detector module uses an object segmentation model to locate conditions present in the at least one dental radiograph.

In another alternative embodiment, the merging module is configured to merge the first and the second outputs such that teeth and conditions are independently viewable by a viewing device. In a further alternative embodiment, the merging module is configured to merge the first and the second outputs such that an individual tooth and an associated condition are viewable by a viewing device.

In another alternative embodiment, the system includes a queue manager to manage operations in the tooth numbering module, condition detector module and the merging module.

In another alternative embodiment, the tooth numbering module uses an object segmentation model to locate and label teeth present in the at least one dental radiograph. In an alternative arrangement, the tooth numbering module is configured with a plurality of tooth numbering models, where each tooth numbering model developed for a particular dental radiograph type.

In another embodiment, a computer-implemented method of analyzing dental radiographs includes receiving at least one dental radiograph, the at least one dental radiograph having a type; analyzing the at least one dental radiograph to locate and label teeth present in the at least one dental radiograph to produce a first output; analyzing the at least one dental radiograph to locate and identify conditions present in the at least one dental radiograph to produce a second output; and, merging the first output from the tooth numbering module and the second output from the condition detector module to form a report having labeled teeth with conditions identified and located on specific teeth.

In an alternative arrangement, the method further includes identifying the type of the at least one dental radiograph. In one alternative arrangement, the type of dental radiograph may be bitewing, periapical, or panoramic. In another alternative arrangement, the method includes using a neural network to analyze the at least one dental radiograph to locate and label teeth further. In a further alternative arrangement, the neural network performs the analysis in a single pass. In a further alternative embodiment, the method further includes creating a report configured to enable an individual tooth and an associated condition to be viewable on a viewing device.

In another embodiment, a non-transitory computer readable storage medium impressed with computer program instructions to analyze dental radiographs, when executed on a processor, implement a method including receiving at least one dental radiograph, the at least one dental radiograph having a type; analyzing the at least one dental radiograph to locate and label teeth present in the at least one dental radiograph to produce a first output; analyzing the at least one dental radiograph to locate and identify conditions present in the at least one dental radiograph to produce a second output; and, merging the first output from the tooth numbering module and the second output from the condition detector module to form a report having labeled teeth with conditions identified and located on specific teeth.

The present invention together with the above and other advantages may best be understood from the following detailed description of the embodiments of the invention illustrated in the drawings, wherein:

DRAWINGS

Figure 1:
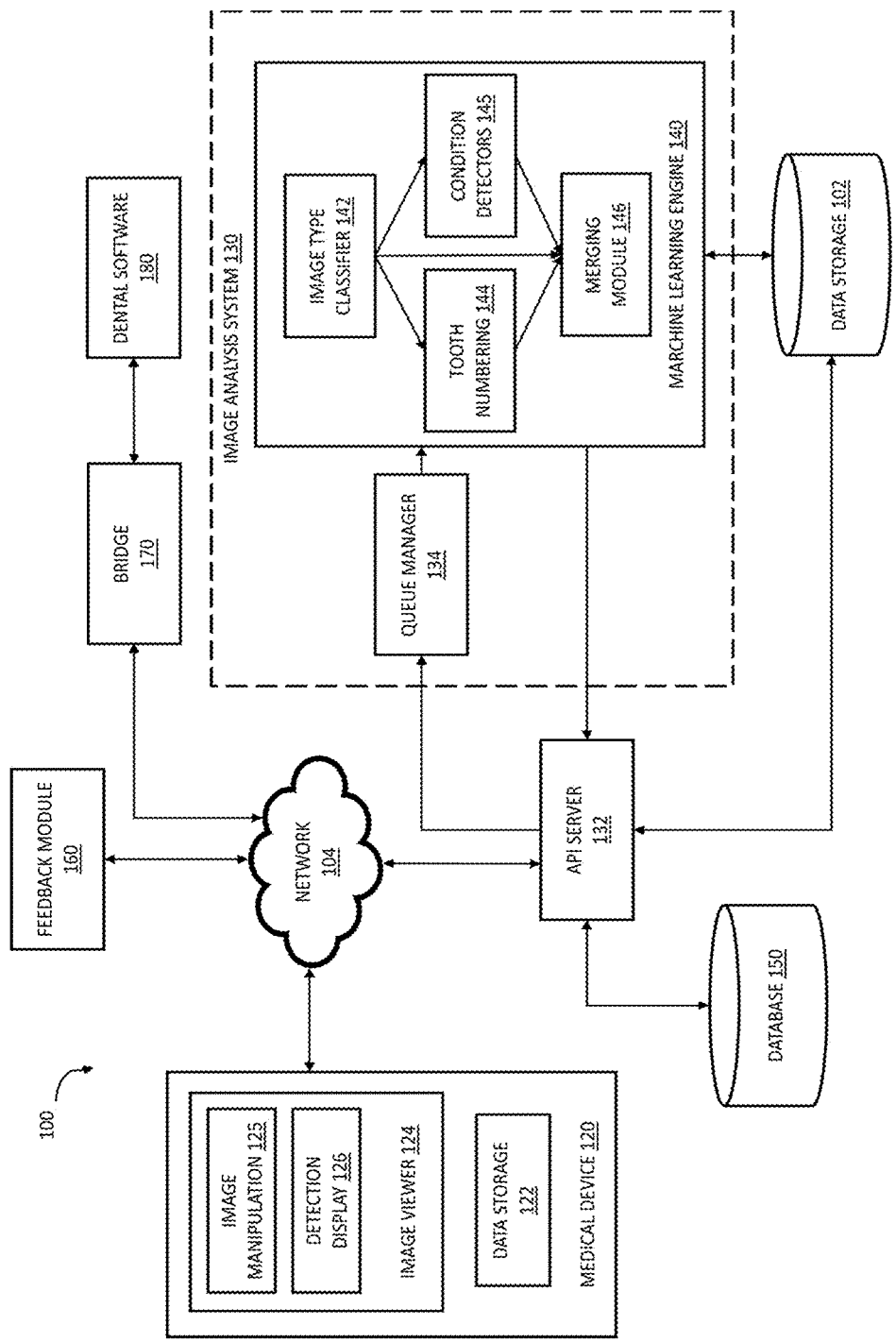
FIG. 1 is a block diagram of an embodiment of the automated radiograph analysis system according to principles of the invention.
Figure 7A:
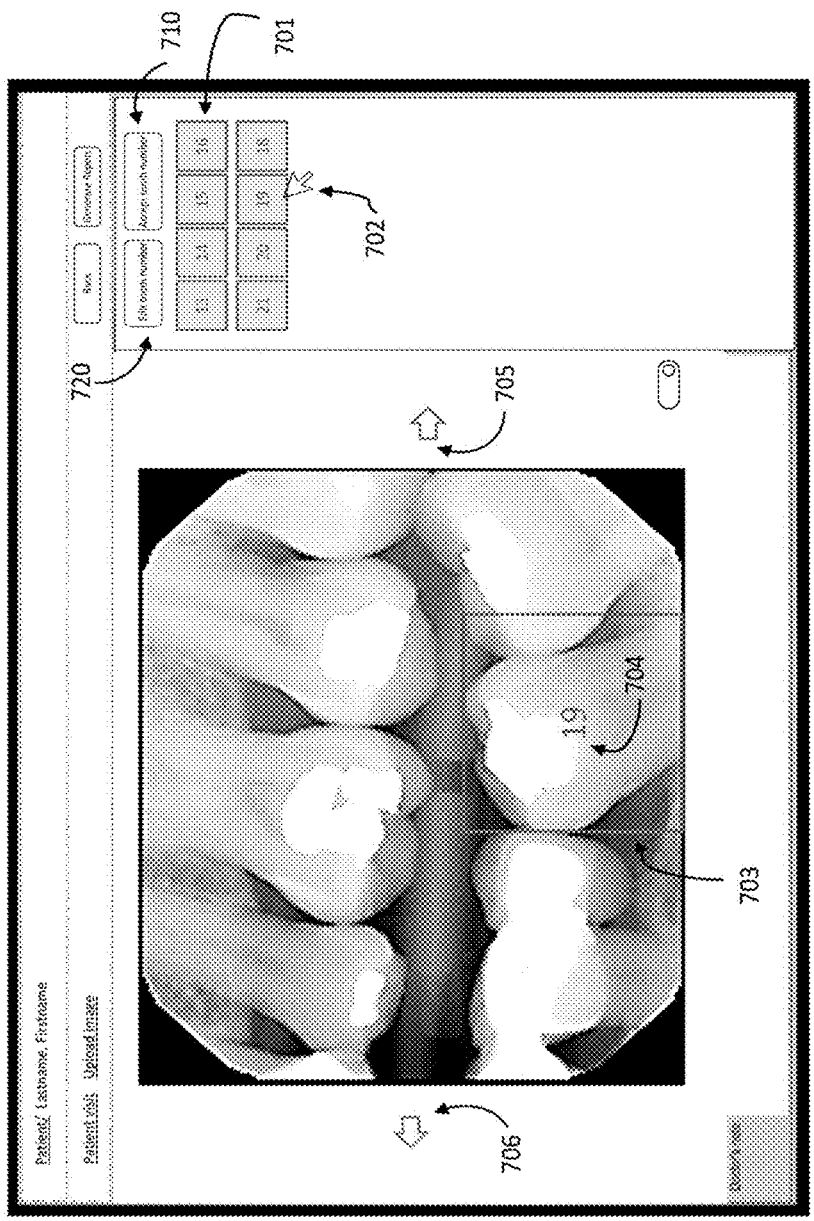
Figure 7B:
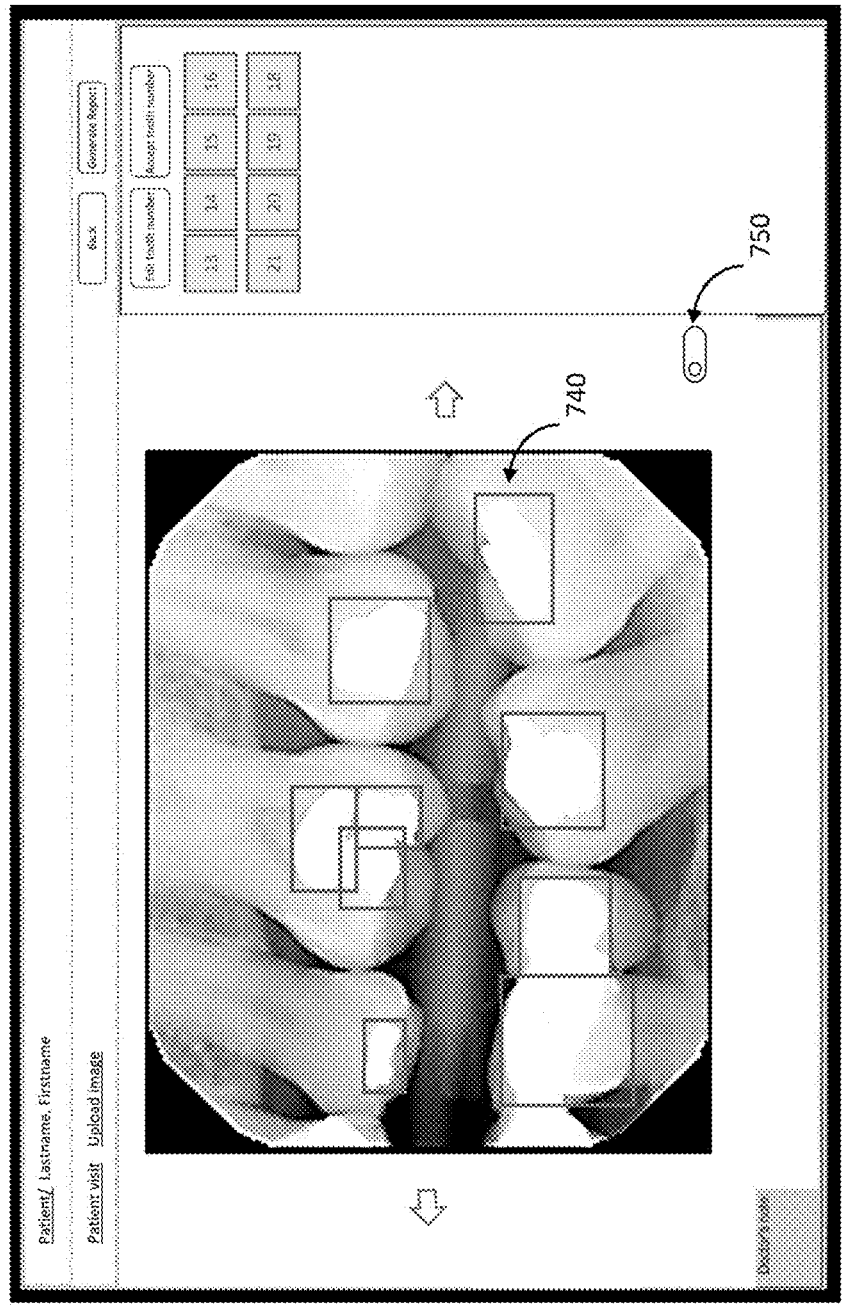
Figure 7C:
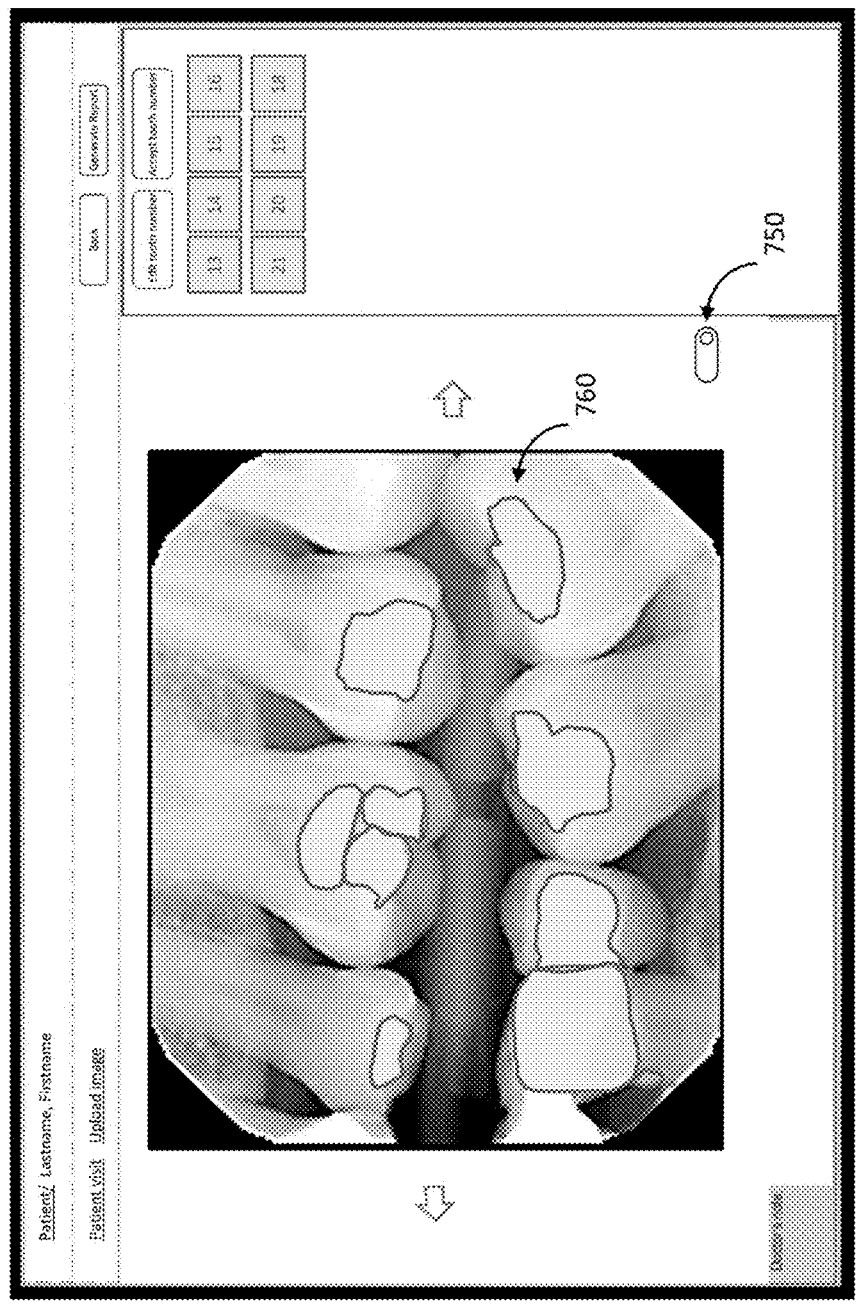
Figure 8:
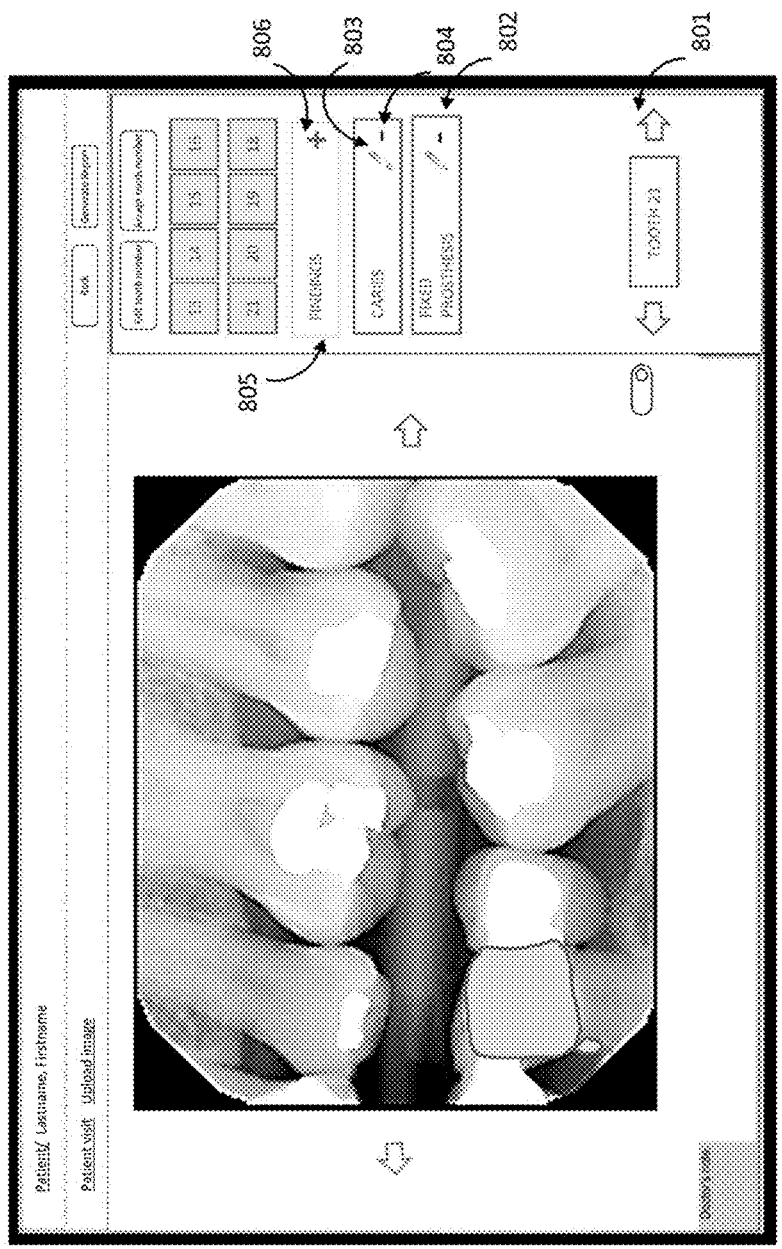

FIG. 7A, FIG. 7B, and FIG. 7C are example visual results of the system of FIG. 1;

FIG. 8 is an example view of the user interface of the system of FIG. 1; and

Figure 9:
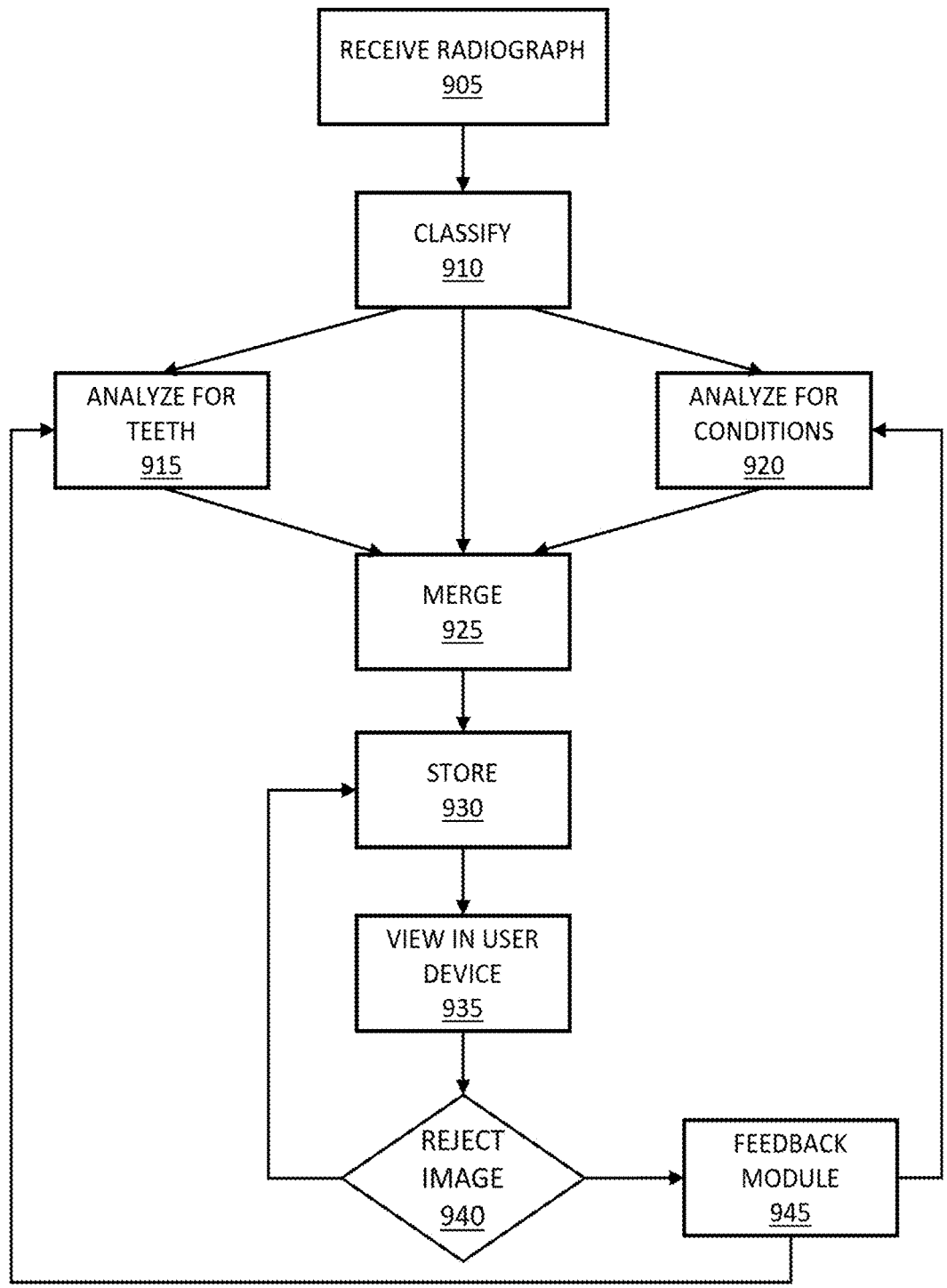

FIG. 9 is a flow chart of the operation of the system of FIG. 1.

DESCRIPTION

The embodiments described herein include methods and systems that use deep neural network architectures, model training procedures and data processing method for automated dental charting and condition detection. The systems and methods produce detailed outputs that are a comprehensive analysis of dental radiographs attributing detected conditions to particular teeth. The systems and methods enable improved performance in successive operation. The systems and methods generate a report consolidating the generated results of radiograph analysis which can be saved in a variety of formats compatible with other healthcare computer systems and application.

Deep learning, a subset of artificial intelligence (AI), enables a computer algorithm to autonomously learn and extract features from input data to model specific phenomena. This capability to learn relevant features from raw input data sets deep learning techniques apart from traditional image processing techniques that typically involve the effort of identifying, handcrafting, and engineering explanatory features.

Models are trained with deep-learning to discern and analyze dental radiographs of various kinds, including but not limited to bitewing, periapical, and panoramic images. The objective is to detect a broad spectrum of dental conditions, anatomies, restorations, and irregularities. The analysis system in place uses the outputs from these trained models to create labeled images. These images, presenting useful diagnostic information, can be displayed to dental professionals via an intuitive user interface.

In one example embodiment, the system capitalizes on machine learning functionalities. The goal is to consistently and automatically detect a wide range of conditions using input radiographic data. Various types of X-ray or radiographic images are marked by subject matter experts during the training phase of the machine learning models. These trained models are then synergistically employed to automatically mark or label radiographs that are received in real-time or near-real-time through an Application Programming Interface (API).

Furthermore, feedback from active users, for instance, practicing dentists, is used to refine the system's performance in identifying different conditions. In certain configurations, a clinician can retrieve a patient's radiographs that are stored on an office server using a medical image viewer application. This application displays interactive interfaces on a network-connected computing system, such as a desktop or laptop.

The Application Programming Interface (API) manages a bridge for interactions and data exchange between various components of the analysis system and external components. A queue management system is also used to pass messages from the API server to the machine learning engine. The API server and the queue manager play roles in processing radiographic files, which are received in a digital format. The API server and the queue manager ensure seamless data transfer to and from an array of machine learning models, some of which are specially designed to recognize an extensive list of dental conditions. The generated image labels resulting from these interactions are then directed to the computing system used by the medical device.

Typically, the patient's radiographic images are captured, transmitted to a cloud-based medical image analysis system for evaluation and annotation via machine learning, and sent back for review within the medical image viewer application. Identified conditions or abnormalities are represented as overlays on the original radiograph within the user interface. These overlays guide the practitioner to the regions of the radiograph that contain the detected conditions or pathologies. The system allows the clinician to edit the display, such as highlighting a particular condition for detailed viewing, via user interface selections.

FIG. 1 is a diagram of an embodiment of the automated radiograph analysis system 100 implemented in a networked computing environment. The system 100 includes an image analysis system 130 with a machine learning engine 140 and a user application for image analysis which in this embodiment is included in a medical device 120. This figure provides an overview of the architecture and the interaction between various components of one embodiment of the automated radiograph analysis system. Those skilled in the art will understand that the system architecture can be implemented in various configurations and should not be considered limited to the specific arrangement shown. The automated radiograph analysis system is designed with Health Insurance Portability and Accountability Act (HIPAA) compliance in mind, ensuring the privacy and security of patient data at all stages of processing.

Within the system 100, a medical device 120 includes an image viewer 124. The image viewer 124 includes an image manipulation element 125, which enables users to visualize an image and adjust several parameters, such as brightness and contrast, invert colors, zoom in on specific areas, and rotate the image. The image viewer 124 also includes a detection display 126, which enables the visualization of the output generated by a machine learning engine 140. The specific features and capabilities of the image viewer 124 provided here are merely exemplary. Other features and capabilities are possible within the scope of the invention.

The medical device 120 also includes a first data storage unit 122, which could be, for example, a hard disk where radiographs are stored and from which users can upload radiographs to the application. The medical device 120 communicates with a network 104. The communication in the present embodiment is through a web browser however other implementations are possible within the scope of the invention.

The medical device 120 communicates over the network 104 with a database 150, an image analysis system 130, and a remote data storage element 102. The database 150 stores application data pertaining to user logins, organization and practice information, patient visits, user findings and patient treatment information. The database 150 further stores the analysis of x-rays done by performed by the image analysis system 130, and doctor's feedback on the analysis. The database 150 is central data repository for all information stored in the networked computing environment 100. This component 150 connects with the API server 132 and provides information required to fulfill a user's request.

The medical device 120 also communicates with one or several remote data storage units 102, such as an Amazon Web Services (AWS) remote disk (S3), or similar services, and also with the image analysis system 130 through an API server 132. The API server 132 coordinates different machine learning algorithms within the machine learning engine 140 with the help of a queue manager 134.

The queue manager 134 coordinates queues to pass messages from the API Server 132 to the machine learning engine 140. Various types of messages that are passed concern, for example, image analysis by different machine learning modules, final image generation with detections, and image manipulation commands. Messages are saved in queue, until they are read. Therefore, if a model server, for example the tooth identification module, is not responding, the messages stay in the queue and are read later when the model server becomes available again. An advantage of the queue manager is that it enables asynchronous processing where the queue manager enables different components of the system to operate independently of each other. As described above, a first component does not have to wait for another component to finish its task before the first component can start its own task. This is particularly useful in a system where tasks can be time-consuming, such as processing and analyzing dental radiographs. Another advantage of the queue manager is load balancing. The queue manager distributes tasks substantially evenly across components or servers, thereby tending to prevent any single component from becoming a bottleneck. This is particularly advantageous in systems that need to handle high volumes of data or requests. Another advantage of the queue manager is fault tolerance. If a particular component fails or crashes, the queue manager's operation tends to maintain tasks which are then re-routed to an alternative component. This makes the system more robust and less prone to data loss. Another advantage of the queue manager is scalability. As the radiograph analysis system grows and the volume of data increases, the queue manager maintains system efficiency by distributing tasks across the increased number of components or servers. Another advantage of the queue manager is managing order and priority of tasks. In sum, the queue manager improves the efficiency, robustness, and scalability of the analysis system.

In various alternative arrangements, queues may be hosted, for example, on Amazon Simple Queue Service (SQS). The queue manager 134 has messages written into it by the API Server and the messages are transmitted to the machine learning engine 140. The machine learning engine 140 reads a message, retrieves an image from the remote data storage 102 and processes the image as required.

The remote data storage 102 and the image analysis system 130 may be hosted on various cloud platforms or, alternatively, on on-premises servers. Communications are encrypted and secure, ensuring HIPAA compliance.

The machine learning engine 140 includes a plurality of modules including an image type classifier 142, a tooth numbering module 144, and a condition detection module 145. The condition detection module 145 includes at least one condition detection model and typically includes more than one condition detection model. The tooth numbering module 144 and the condition detection module 145 operate independently of each other. Each module 144, 145 is coordinated by the API server 132 and the queue manager 134.

The machine learning engine 140 further includes a merging module 146 that combines the results from the different machine learning tasks. It receives the results of tooth numbering module 144 and different condition detectors 145 and performs a processing to associate each condition to its corresponding tooth. This feature provides an intuitive format to be used for processing detections on the image viewer 124.

The image viewer 124 communicates over the network 104 with a feedback module 160 through the API server 132 to further enhance performances of models in the machine learning engine 140. When the generated outputs of machine learning are received from image analysis system 130, the user can reject the analysis. The rejection triggers a feedback loop to an external system for manual annotation. Dental experts review the outputs and apply changes if needed, then import the annotated analysis to a training dataset. This feedback improves the model performances after retraining.

The networked computing system 100 also incorporates a bridge 170. The bridge 170 is a module for interfacing with third-party services and with dental Practice Management Systems (PMS). The bridge includes connections with dental PMS/Imaging systems, data aggregation services like Sikka, and third-party platforms such as GuideMia. The bridge 170 functions as a conduit facilitating communication between the API Server 132 and external dental software solutions 180.

In addition to the above, the networked computing environment 100 has been designed with the principles of "security by design" in mind. Security considerations are integrated into every stage of the system's design and operation. This includes measures to prevent unauthorized access to user information, maintain the integrity and reliability of the system, and provide assurances of its availability. The networked computing environment 100 also includes measures to ensure that it can adapt to new threats and vulnerabilities as they emerge, ensuring ongoing compliance with HIPAA and other relevant regulations.

Figure 2:
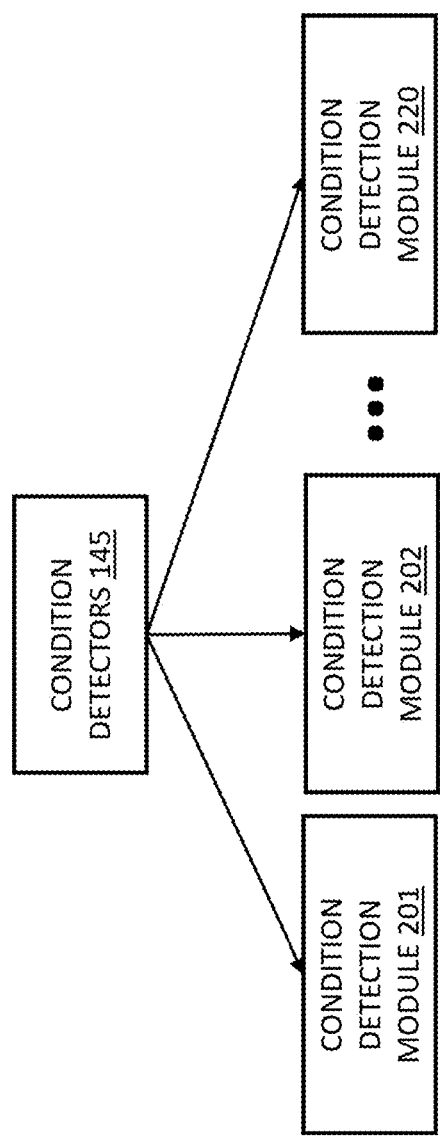
FIG. 2 is a block diagram of the condition detection module of FIG. 1.

FIG. 2 is a block diagram of the condition detection module 145. The condition detection module includes a plurality of condition detection models 201, 202, 220, also referred to as "condition detectors". The condition detection module 145 uses machine learning techniques to identify and classify a plurality of dental pathologies and conditions. Each model 201, 202, 220 in the condition detection module 145 is developed for a specific set of tasks and operates to detect a specific condition or pathology.

The models 201, 202, 220 within the condition detection module 145 are trained and optimized to detect and classify various dental conditions in dental radiographs. The models 201, 202, 220 provide a precise location of the detected conditions in the form of a mask covering the detected finding and/or a bounding box, which is a rectangle surrounding the detected condition. Masks and bounding boxes can be provided together, and the user is provided with the flexibility to switch between the two visualizations. The use of object segmentation techniques enables a detailed and precise analysis, enhancing the accuracy and usability of the system. In object segmentation, the pixels forming an object are detected and grouped as an object of interest.

The condition detection module 145 uses object detection and segmentation models, such as the YOLO (You Only Look Once) series, for identifying and localizing dental conditions in radiographs. These conditions can be both pathological, such as caries, pulpal involvement, and attrition, and non-pathological, such as implants and restorations. It should be noted that the conditions detected by the present system are not limited to those listed here.

The object detection model used in this embodiment is, for example, YOLOv8. YOLOv8 is a model that can be used for object detection, image classification, and instance segmentation tasks. It was developed and open-sourced by Ultralytics, Inc. YOLOv8 generally outperforms other known models both in accuracy and execution time on large computer vision tasks. YOLOv8 uses a single neural network to perform both classification and prediction of bounding boxes and masks for detected objects, optimizing for detection performance. As a segmentation model, YOLOv8 outputs a pixel-level mask for each detected object, providing a more precise localization of the object within an image.

The YOLOv8 model has three main components for making predictions: a backbone, a neck, and a head. The backbone, a deep learning architecture based on convolutional neural networks (CNNs), is responsible for feature extraction from input images. The neck works as a feature aggregator, collecting features from different stages of the backbone. The head, also referred to as the object detector, takes features from the neck and performs localization and classification of different conditions. Each condition is then located in the image by a mask, a rectangular bounding box, and its class.

In this embodiment, a plurality of YOLOv8 models have been trained, each on one of a plurality of conditions. Each model outputs pixel-level masks for each detected condition on an input radiograph, along with a class label indicating the condition and a bounding box. These models operate asynchronously and the resulting outputs, along with the output of the tooth numbering model, are passed to the merging module 146 to provide the final output.

The tooth numbering module 144, which uses an object segmentation model, uses advanced deep learning techniques to locate each tooth in a dental radiograph. The tooth number module 144 takes an input dental image and generates masks that group all pixels of each tooth. The tooth numbering module 144 outputs corresponding teeth numbers. Although the illustrative figures use the Universal Numbering System, other numbering systems can also be accommodated within the scope of the invention.

In the present embodiment, both Mask R-CNN and YOLOv8 segmentation models are used, but the system and methodologies of the present invention are not limited to these specific models or object detectors.

Mask R-CNN is a type of Deep Learning architecture for image analysis called Convolutional Neural Networks (CNNs). It outputs a class label, a bounding box, and a corresponding mask (set of pixels) for each candidate object. Mask R-CNN consists of three components: i) a deep fully convolutional network that proposes regions, called a Region Proposal Network (RPN), ii) a detector that extracts features using RoIPool (Region of Interest Pooling) from each candidate box and performs classification and bounding-box regression, and iii) predicting segmentation masks on each Region of Interest (RoI) at the pixel level.

The specific design and implementation of these models can be adapted and extended according to the requirements of the application. The use of object segmentation techniques allows for a detailed and precise analysis, enhancing the accuracy and usability of the system. The models work in tandem to provide a comprehensive and accurate analysis of dental radiographs.

The image type classifier 142, also referred to as the image type classification module, is a component of the machine learning engine 140, shown in FIG. 1. This module uses a Convolutional Neural Network (CNN), which is a class of deep learning models, to classify the types of dental radiographs. The CNN is designed to automatically and adaptively learn spatial hierarchies of features from the input dental radiographs.

The CNN model used in the image type classification module 142 is trained to recognize and classify different types of dental radiographs such as bitewing, periapical, and panoramic images. The model takes as input a dental radiograph and outputs the type of the radiograph. This radiograph type classification is used in the subsequent steps of tooth numbering and condition detection, as the strategies for these tasks may vary depending on the type of the radiograph.

The CNN model used for image type classification consists of multiple layers, including convolutional layers, pooling layers, and fully connected layers. The convolutional layers are responsible for extracting features from the input image, the pooling layers reduce the spatial size of the extracted features to reduce the computational complexity, and the fully connected layers perform the final classification based on the extracted and pooled features.

The outputs of the image type classification module 142 trigger appropriate models to be launched in the tooth numbering module 144 and the condition detection module 145. The appropriate models depend on the type of the input radiographs. For example, if the input radiograph is classified as Panoramic, panoramic tooth numbering and panoramic condition detectors are launched. This output is also used by the merging module to indicate the appropriate type for the image viewer 124.

The specific architecture and parameters of the CNN model can be adapted and optimized according to the requirements of the application. The model is trained and fine-tuned on a large dataset of labeled dental radiographs to achieve high classification accuracy.

While a CNN is used in the present embodiment for image type classification, the systems and methods of the present invention are not limited to this specific model or any particular type of deep learning model. Other types of machine learning algorithms are possible within the scope of the invention.

Training Data Collection

In one embodiment of the present invention, the process of data collection and annotation is meticulously carried out to ensure the precision and reliability of the training data. This process is a part of the development of the machine learning models used in the system 100, as the quality and accuracy of the training data directly influence the performance of the models.

The training data is generated through a series of reviews conducted by multiple dental professionals, which may include dentists and radiographers. These professionals are provided with a specialized annotation tool that facilitates the process of marking and labeling dental radiographs for relevant conditions The annotation tool is designed with a user-friendly interface that allows the annotators to draw bounding boxes or polygons around each present tooth and each identified condition or anatomy. The tool also includes features for adding any kind of metadata that may be necessary for identifying the dental conditions. To assist the annotators in focusing on one type of annotation at a time, the tool provides the option to show and hide annotations.

The annotators work with a list of anonymized radiographs, processing each image individually. To expedite the annotation process, one or multiple models may be trained on a subset of already annotated images. These models may be used to process other non-annotated images and generate initial annotations in a format acceptable by the annotation tool. Annotators may start from these initial annotations and make necessary updates, thereby speeding up the annotation process.

The annotation tool is capable of generating the resulting annotations in several formats. These formats contain coordinates of polygons, bounding boxes, and all associated metadata information. The specific design and implementation of the annotation tool may be adapted and extended according to the requirements of the application.

This detailed and rigorous process of data collection and annotation enable the creation of a high-quality training dataset. This dataset is instrumental in training the machine learning models to accurately classify image types, number teeth, and detect dental conditions, thereby enhancing the overall performance and usability of the system.

Model Training and Evaluation

The training process of the machine learning engine 140 models involves the use of collected data described above. The annotated images are used to train the models, each model tailored for a specific set of tasks.

During the training process, a series of tests may be conducted to select the best hyperparameters for each model. Hyperparameters are parameters that are not learned from the data during the training process, but are set prior to the training process. They control the learning process of the model and can significantly impact the performance of the model. Examples of hyperparameters include the learning rate, the number of layers in the neural network, the number of units in each layer, and the type of optimizer used for training.

Once the models are trained, they are evaluated using a subset of images that were not used during the training process. This subset of images is independent from the training process and is used to test the performance of the models. The performance of the models is measured using a list of metrics, which include Precision, Recall, Accuracy, F1 Score, Sensitivity, and Specificity using the formulas:

$$\text{Precision} = TP/(TP+FP)$$

$$\text{Recall} = TP/(TP+FN)$$

$$\text{Accuracy} = (TP+TN)/(TP+FP+TN+FN)$$

$$F1 = (2 \times \text{Precision} \times \text{Recall})/(\text{Precision}+\text{Recall})$$

$$\text{Sensitivity} = \text{Recall} = TP/(TP+FN)$$

$$\text{Specificity} = TN/(TN+FP)$$

where: True Positives (TP) are instances where the model correctly identifies the presence of a condition; False Positives (FP) are instances where the model incorrectly identifies the presence of a condition; True Negatives (TN) are instances where the model correctly identifies the absence of a condition; and False Negatives (FN) are instances where the model incorrectly identifies the absence of a condition.

In the context of segmentation or object detection, Intersection over Union (IoU) is used to compute TP, FP, TN, and FN. IoU is the area of overlap between the predicted segmentation and the ground truth divided by the area of union between the predicted segmentation and the ground truth. If the IoU is above a certain threshold, the prediction is considered a TP; if below, it is considered a FP. TN and FN are calculated similarly.

The precision measures the proportion of positive identifications that were actually correct. The recall measures the proportion of actual positives that were identified correctly. The accuracy measures the proportion of all classifications that were correct. The F1 Score is the harmonic mean of Precision and Recall and provides a balance between these two metrics. Sensitivity is another term for Recall. Specificity measures the proportion of actual negatives that were identified correctly.

These metrics, among others, when used together, provide a comprehensive view of the model's performance, taking into account both its successes (TP and TN) and its failures (FP and FN).

Figure 3:
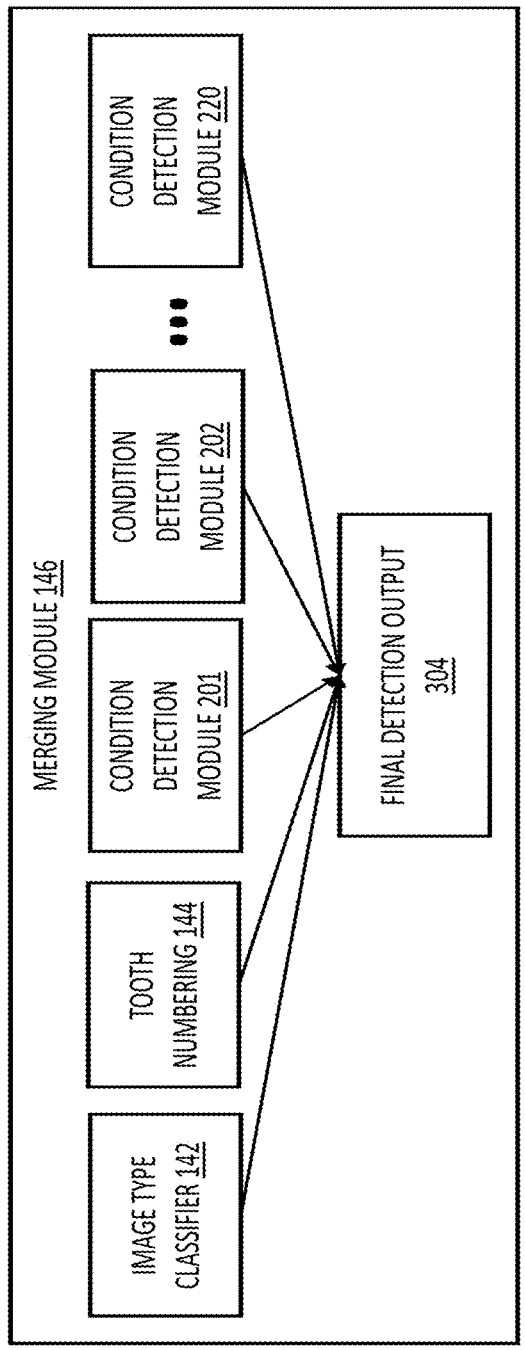
FIG. 3 is a block diagram illustrating the data flow of the merging module of FIG. 1.

FIG. 3 is a block diagram illustrating the data flow of the merging module 146 in the machine learning engine 140 of FIG. 1. The merging module 146 is designed to integrate the outputs of the tooth numbering module 144 and the condition detectors 201, 202, . . . , 220, and the image type classifier 142.

As described above, the tooth numbering module 144 uses an object segmentation model to identify and classify teeth in a dental radiograph. It provides a detailed mask or polygon that covers each tooth, along with the correct tooth number according to a recognized notation system.

The models 201, 202, . . . , 220 within the conditions detection module 145 provide detailed masks or polygons covering the detected findings, and/or bounding boxes surrounding each detected condition.

The merging module 146 takes these detailed outputs and combines them to create a comprehensive analysis of the dental radiograph, where each condition, if it belongs to a tooth, is attributed to its respective tooth. The final detection output 304 is then communicated to the image viewer 124. This output includes the type of the processed radiograph, the location and classification of each tooth, along with the location and classification of any detected condition.

The merging module 146 combines the outputs from the different models accurately and presents the output of that combining process in a user-friendly format. This integrated approach enables a comprehensive and detailed analysis of dental radiographs, enhancing the overall functionality and usability of the system.

Figure 4:
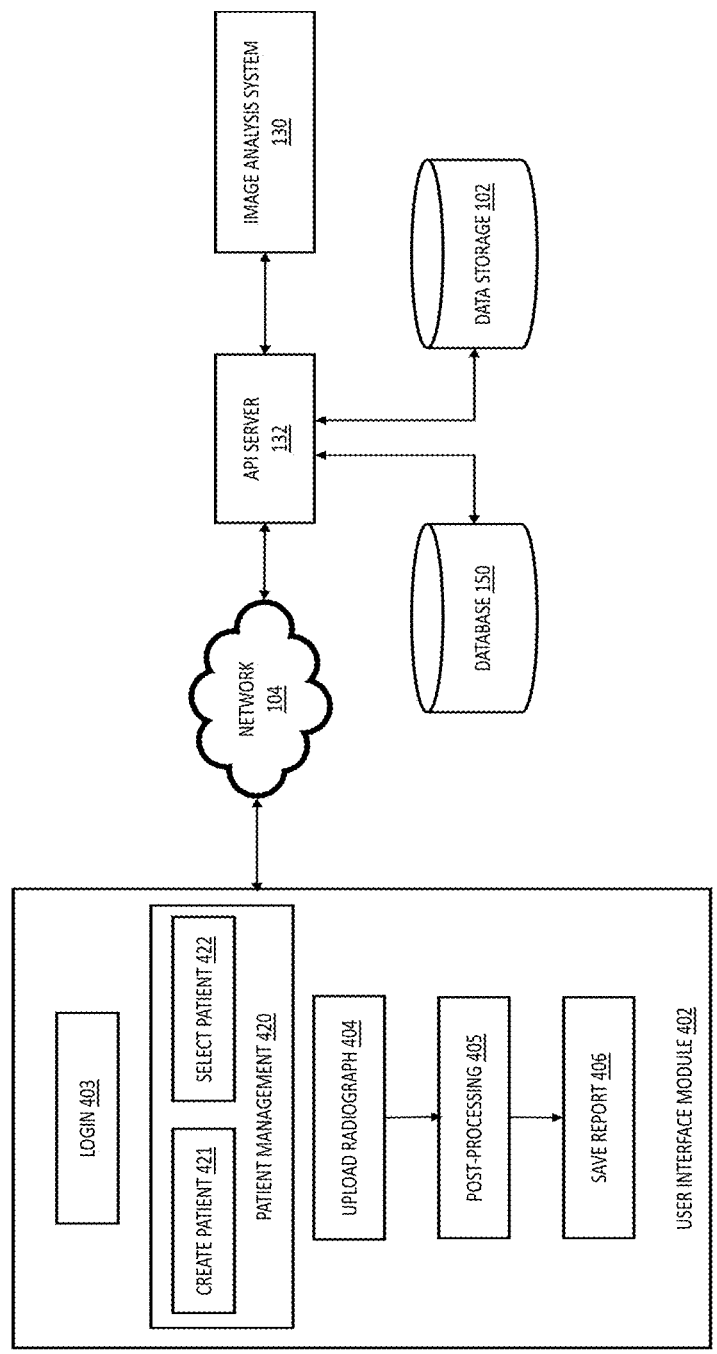
FIG. 4 is a block diagram of a portion of the system shown in FIG. 1 also showing the communication between the user interface module and the image analysis system.

FIG. 4 is a block diagram of a portion of the system shown in FIG. 1. FIG. 4 illustrates the communication between the user interface module 402 and the image analysis system 130. This communication begins with the initial step of uploading the radiograph 404 and concludes with the final step of saving a report 406.

The user interface 402 is equipped with a login section 403, which allows users to securely access the system. Once logged in, users can interact with the patient management system 420. This system provides options to select an existing patient 421 or create a new patient 422. This information is communicated with the database 150 through the API server 132.

The user interface 402 also facilitates the uploading 404 of one or more radiographs. These radiographs can be uploaded from local storage devices, for example. The system 100 is designed to handle a variety of image formats, ensuring compatibility with different radiographic imaging technologies.

Post-processing 405 is another feature of the user interface 402. This feature provides users with a set of tools to add, remove, or edit one or multiple teeth, and one or multiple findings. These tools enable users to refine the analysis results, ensuring that the final output accurately represents the patient's dental condition.

The final step in the sequence is saving a report 406. This report consolidates all the generated results for all uploaded radiographs. It also includes a documentation of different possible findings for educational purposes. This report can be saved in various formats and shared with patients or other healthcare professionals, facilitating informed decision-making regarding the patient's dental health.

Figure 5A:
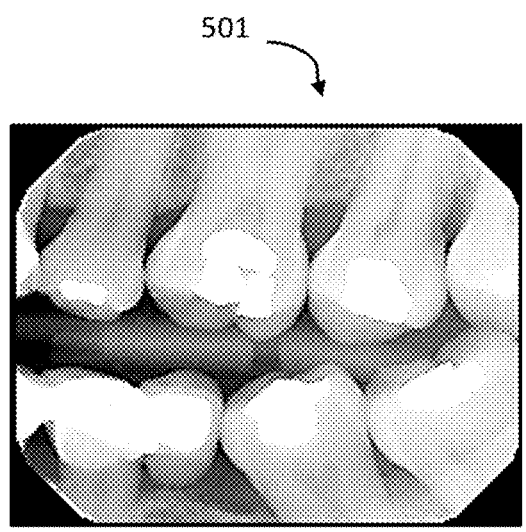
FIG. 5A, FIG. 5B and FIG. 5C are example dental radiographs suitable for use with the system of FIG. 1.
Figure 5B:
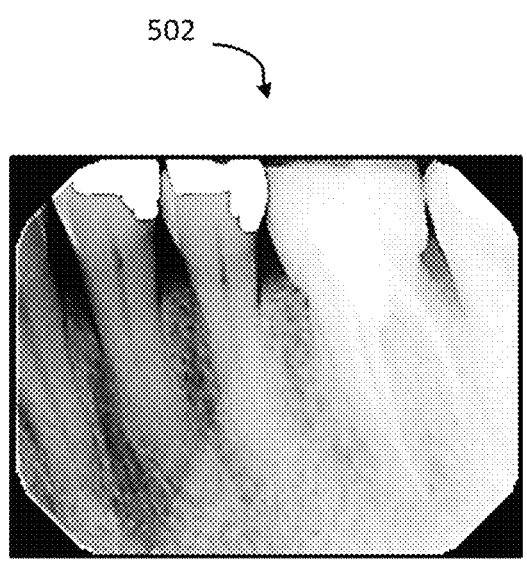
Figure 5C:
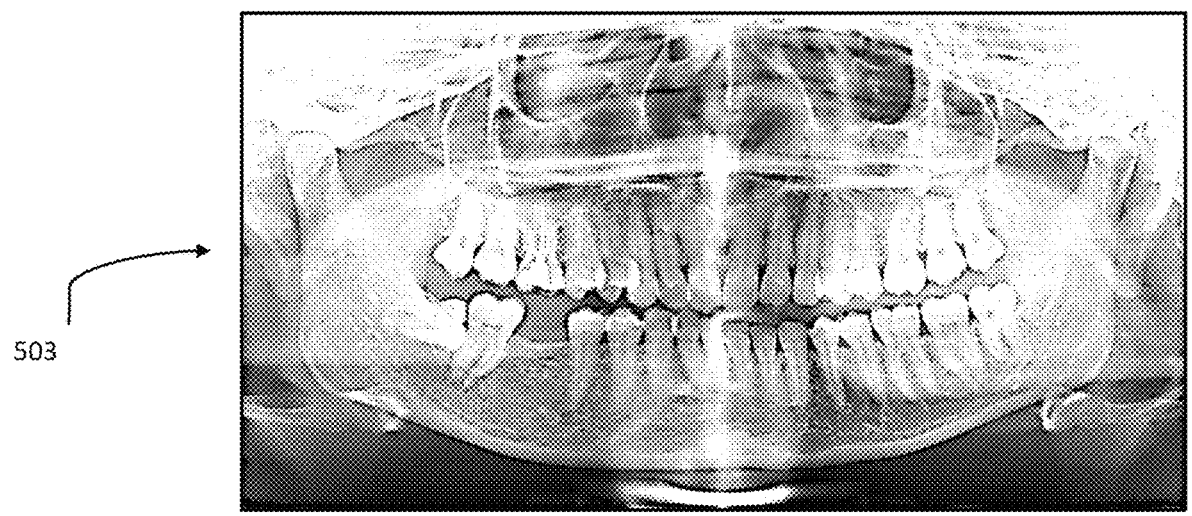

FIG. 5A, FIG. 5B and FIG. 5C are examples of three types of dental radiographs supported by the system. These radiographs include Bitewing radiograph 501 (FIG. 5A), Periapical radiograph 502 (FIG. 5B), and Panoramic radiograph 503 (FIG. 5C).

The Bitewing radiograph 501 of FIG. 5A is a type of dental X-ray that is typically used to check for cavities between teeth. It provides a clear view of the upper and lower teeth in a single shot, making it a valuable tool for detecting decay and changes in bone density.

The Periapical radiograph 502 of FIG. 5B, on the other hand, is used to examine the entire tooth, from the crown to the root and the surrounding bone structure. It is particularly useful for identifying any abnormalities in the root structure and surrounding bone tissue.

Lastly, the Panoramic radiograph 503 of FIG. 5C provides a broad view of the entire mouth, capturing all teeth, upper and lower jaws, and surrounding structures and tissues in a single image. This type of radiograph is often used for planning treatments, such as implants, extractions, braces, and dentures.

The system 100 is designed to handle and analyze these different types of radiographs, demonstrating its versatility and wide applicability in various dental diagnostic scenarios.

Figure 6:
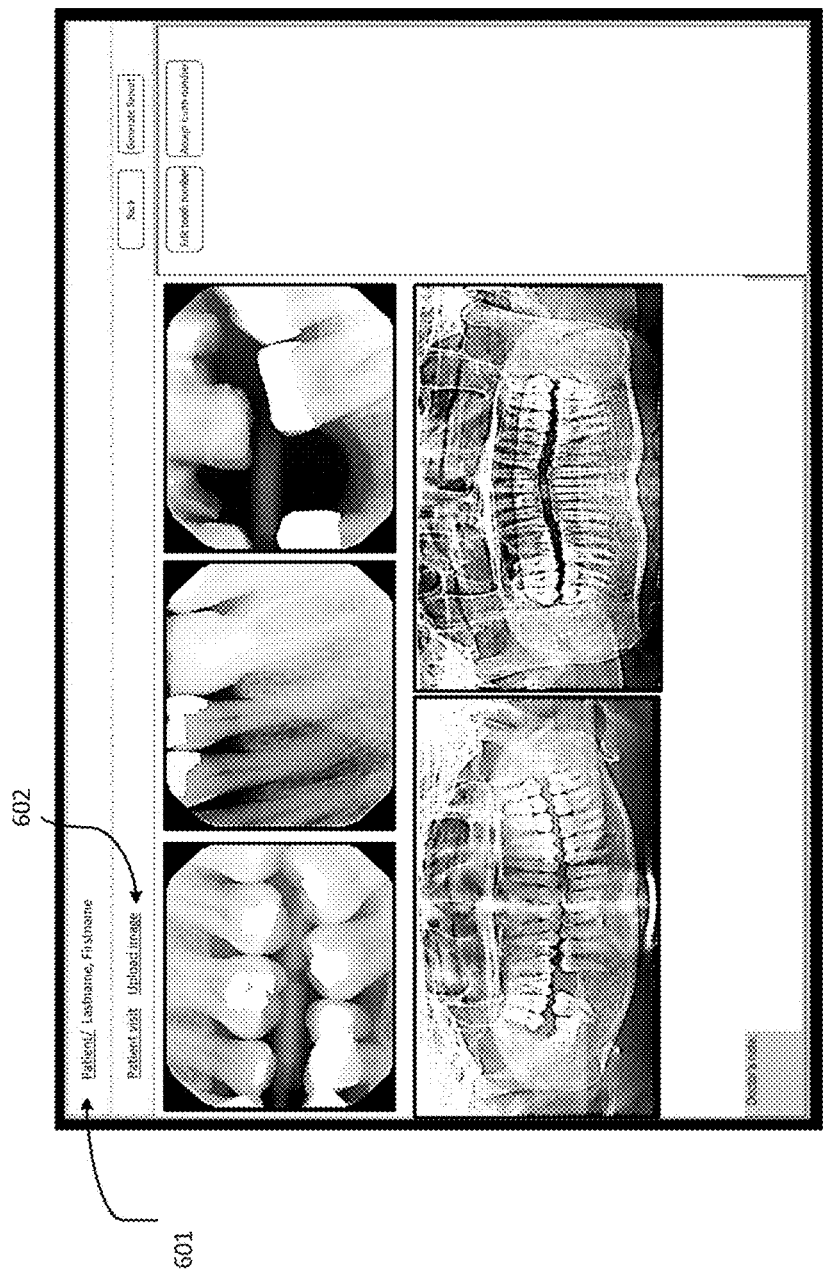
FIG. 6 is an example view of the user interface of the user interface module of FIG. 4.

FIG. 6 illustrates the user interface module 402, specifically focusing on the feature for uploading radiographs. This figure provides a visual representation of the user experience during the initial step of the image analysis process.

The interface displays the patient's name 601. A dedicated button 602 is provided for the user to upload one or multiple radiographs. This feature is designed to be user-friendly and efficient, allowing for easy navigation and operation.

Additionally, the user can manually select the type of the radiograph from a predefined list. However, the system 100 is equipped with a machine learning algorithm 142 that automatically processes the uploaded radiograph to accurately determine its type. This automated feature enhances the system's usability and efficiency, reducing the need for manual input and potential errors.

FIG. 7A shows the interactive feature of the system 100, specifically focusing on the visualization of tooth numbering. This figure demonstrates the user's ability to review and approve the tooth numbering before proceeding to the next step of pathology visualization and post-processing.

When a radiograph is processed by the image analysis system 130, the list of detected teeth is communicated through the network 104 and displayed to the user on a panel 701. As the user hovers over a tooth number on the panel 701 using the mouse 702, a bounding box 703 is drawn around the corresponding tooth on the radiograph displayed on the image viewer 124. The number of the tooth 704 is also displayed on the detected tooth, providing a clear and intuitive visualization for the user.

The user interface module 402 provides the user with the ability to edit the tooth numbering 720 or accept it 710. The editing feature allows the user to add a tooth by drawing a polygon around the tooth and specifying its number, remove a tooth, or change the number of a tooth. This interactive feature ensures that the system's output aligns with the user's understanding and expectations, enhancing the accuracy and usability of the system.

Additionally, the user interface module 402 includes navigation arrows 705 and 706, enabling the user to move to the next or previous radiograph. This feature allows for efficient navigation through multiple radiographs, enhancing the user experience.

FIG. 7B and FIG. 7C are illustrations that demonstrate the system's capability to visualize detected pathologies in two distinct formats.

In FIG. 7B, the system displays the detected pathologies in the form of bounding boxes 740. Each bounding box is a rectangle that surrounds a detected finding, providing a clear and concise visual representation of the location and extent of the pathology. This visualization format is particularly useful for providing a quick overview of the detected pathologies.

In FIG. 7C, the system displays the detected pathologies in the form of masks 760. Each mask precisely covers a detected finding, providing a more detailed and accurate visualization of the pathology. This format is especially beneficial for a more in-depth analysis of the detected pathologies.

The user interface provides a switch 750 that allows the user to easily toggle between these two visualization formats. This feature provides flexibility to the user, allowing them to choose the visualization format that best suits their needs and preferences. When the user is not hovering over any tooth number on the panel 701, the system defaults to displaying the conditions in the selected visualization format.

FIG. 8 is an illustration that demonstrates the interactive feature of the system, which enables the user to visualize and manage the detected pathologies for a selected tooth after the final tooth numbering has been accepted. This figure highlights the system's ability to provide a personalized and accurate analysis by enabling the user to add, remove, or correct the list of findings.

Once the final tooth numbering is accepted, the system displays a list of detected findings for each tooth on a dedicated panel 805. A separate panel 801 shows the currently selected tooth, with arrows allowing the user to navigate between different teeth.

For each detected finding listed in panel 805, the user has the option to edit it using an edit button 803 or reject it using a reject button 804, 802. Editing a finding allows the user to change its name or adjust its location on the radiograph.

Additionally, the user has the ability to add a new finding to the current tooth using an add button 806. This feature allows for a more comprehensive and personalized analysis by enabling the user to include additional findings that may not have been initially detected by the system.

The detected findings associated with the currently selected tooth are visualized on the image viewer in the form of a mask or a bounding box, depending on the user's preference set by the toggle button 750. If the user hovers over a specific finding in the panel 805, only that finding is displayed on the image viewer, providing a focused view of the selected pathology.

FIG. 9 is a flow chart of the operation of the system of FIG. 1. At step 905, the image analysis system received at least one radiograph to analyze. As described above, images for analysis are stored in one or more storage devices and typically a user selects the radiograph or radiographs to be analyzed through a user interface.

At step 910, the image type classifier in the image analysis system determines the type of radiograph it has received, such as bitewing, periapical, and panoramic. This module uses a Convolutional Neural Network (CNN), which is a class of deep learning models, to classify the types of dental radiographs. The CNN is configured to automatically and adaptively learn spatial hierarchies of features from the input dental radiographs. The model takes as input a dental radiograph and outputs the type of the radiograph. This radiograph type classification is used in the subsequent steps of tooth numbering and condition detection.

At step 915, the tooth numbering module receives the radiograph and the information about its classification. The tooth numbering module uses object segmentation models and uses advanced deep learning techniques to locate each tooth in a dental radiograph. The particular model used by the tooth numbering module depends on the type of radiograph. The tooth numbering module analyzes the radiograph and locates the teeth and outputs locations with corresponding teeth numbers. The number system is, for example, the Universal Numbering System, also known as the "American System".

At step 920, condition detector also receives the radiograph and the information about its classification from the classifier module. The condition detection module uses object detection and segmentation models to identify and localize dental conditions in the radiograph. These conditions can be both pathological, such as caries, pulpal involvement, and attrition, and non-pathological, such as implants and restorations. The condition detector develops both masks and bounding boxes for the conditions.

At step 925, merge module receives as input the analyses of the radiograph output by the tooth numbering module and the condition detector module. The tooth numbering module and the condition detector module operate independently in parallel. The merging module takes the tooth numbering module and condition detector module outputs and combines them to create a comprehensive analysis of the dental radiograph. In the comprehensive analysis, each condition, if it belongs to a tooth, is attributed to its respective tooth or alternatively to two teeth if the condition is located between teeth. Conditions which are not located on any tooth are generally treated as false positives.

At step 930, the analysis of the radiograph is stored for use by the medical device image viewer.

At step 935, user calls up report or other results including the analyzed radiograph.

At step 940, the user has the option of accepting or rejecting the analyzed radiograph. The user may also annotate to rejected analyzed radiograph and provide reasons for rejection. The rejected radiograph is sent to the feedback module.

At step 945, feedback module receives the rejected radiograph and additional information from the user. The feedback module operates in various ways to process the radiograph and information. The results are used to update the models used by the classifier, the tooth number module and the condition detecting module. This helps to maintain the accuracy of the analysis system and also helps to improve its performance.

It is to be understood that the above-identified embodiments are simply illustrative of the principles of the invention. Various and other modifications and changes may be made by those skilled in the art which will embody the principles of the invention and fall within the spirit and scope thereof.

We claim:

1. A system for analyzing a dental radiograph, comprising:
   a processor; and
   a memory coupled to the processor, the memory having instructions stored thereon, which when executed by the processor, cause the system to:
   receive at least one dental radiograph;
   locate and label teeth present in the at least one dental radiograph using a first machine learning model to produce a first output;
   locate and identify a condition in the at least one dental radiograph using a second machine learning model to produce a second output;
   manage a queue of operations in a machine learning engine to enable asynchronous processing between the first machine learning model and the second machine learning model within the machine learning engine, wherein the operations include image analysis messages, image generation messages, and image manipulation commands; and
   merge the first output and the second output to generate a report, the report including labeled teeth with identified conditions located on specific teeth, wherein the labeled teeth and the identified conditions are located with a polygon and a mask.

2. The system of claim 1, wherein the instructions, when executed by the processor, further cause the system to:
   automatically determine a type of the at least one dental radiograph using a third machine learning model.

3. The system of claim 1, wherein after merging the first output and the second output, the labeled teeth and the identified conditions are independently viewable by a viewing device.

4. The system of claim 1, wherein after merging the first output and the second output, an individual tooth and an associated condition are viewable by a viewing device.

5. The system of claim 1, wherein the first machine learning model includes an object segmentation model configured to locate and label each individual tooth of the teeth present in the at least one dental radiograph.

6. The system of claim 5, wherein the first machine learning model includes a plurality of object segmentation models, each object segmentation model developed for a particular dental radiograph type.

7. The system of claim 5, wherein the object segmentation model includes at least one of a Mask Region-based Convolutional Neural Network (Mask R-CNN) or a You Only Look Once (YOLO) segmentation model.

8. The system of claim 1, wherein the second machine learning model includes a plurality of models, each model developed for a particular dental radiograph type.

9. The system of claim 8, wherein the plurality of models includes an object detection model configured to identify conditions present in the at least one dental radiograph.

10. The system of claim 9, wherein the plurality of models includes an object segmentation model configured to locate the conditions present in the at least one dental radiograph.

11. The system of claim 1, wherein the condition includes at least one of pulpal involvement or attrition associated with the teeth.

12. The system of claim 1, wherein the instructions, when executed by the processor, further cause the system to:
receive a rejection by a user, the rejection configured to trigger a feedback loop to an external system to perform an analysis of the report, wherein the rejection includes a manual annotation and a reason for the rejection; and
import an analysis of the report to a training dataset to retrain the first machine learning model and the second machine learning model.

13. The system of claim 1, further comprising:
training the first machine learning model and the second machine learning model, wherein a series of tests are performed to select hyperparameters for each of the first machine learning model and the second machine learning model, and
wherein the hyperparameters include at least one of a learning rate, a number of layers, a number of units in each layer of the layers, or a type of optimizer.

14. A computer-implemented method of analyzing dental radiographs, comprising:
receiving at least one dental radiograph;
analyzing the at least one dental radiograph to locate and label teeth present in the at least one dental radiograph using a first machine learning model to produce a first output;
analyzing the at least one dental radiograph to locate and identify conditions present in the at least one dental radiograph using a second machine learning network model to produce a second output;
manage a queue of operations in a machine learning engine to enable asynchronous processing between the first machine learning model and the second machine learning model within the machine learning engine, wherein the operations include image analysis messages, image generation messages, and image manipulation commands; and
merging the first output and the second output to generate a report, the report including labeled teeth with identified conditions located on specific teeth, wherein the labeled teeth and the identified conditions are located with a polygon and a mask.

15. The computer-implemented method of claim 14, further comprising:
automatically determining a type of the at least one dental radiograph using a third machine learning model.

16. The computer-implemented method of claim 15, wherein the type of the at least one dental radiograph includes at least one of a bitewing radiograph, a periapical radiograph, or a panoramic radiograph.

17. The computer-implemented method of claim 14, wherein the first machine learning model includes an object segmentation model, and wherein analyzing the at least one dental radiograph to locate and label teeth further includes using a neural network of the object segmentation model for the analysis in a single pass.

18. The computer-implemented method of claim 14, wherein the report is configured to enable an individual tooth and an associated condition to be viewable on a viewing device.

19. A non-transitory computer readable storage medium including instructions that, when executed by a processor, cause the process to perform a computer-implemented method of analyzing dental radiographs, the method comprising:
receiving at least one dental radiograph;
analyzing the at least one dental radiograph to locate and label teeth present in the at least one dental radiograph using a first machine learning model to produce a first output;
analyzing the at least one dental radiograph to locate and identify conditions present in the at least one dental radiograph using a second machine learning model to produce a second output;
manage a queue of operations in a machine learning engine to enable asynchronous processing between the first machine learning model and the second machine learning model within the machine learning engine, wherein the operations include image analysis messages, image generation messages, and image manipulation commands; and
merging the first output and the second output to generate a report, the report including labeled teeth with identified conditions located on specific teeth, wherein the labeled teeth and the identified conditions are located with a polygon and a mask.

* * * * *